United States Patent
Guskey et al.

(10) Patent No.: US 9,622,951 B2
(45) Date of Patent: Apr. 18, 2017

(54) PERSONAL CARE COMPOSITIONS

(71) Applicant: The Procter & Gamble Company, Cincinnati, OH (US)

(72) Inventors: Gerald John Guskey, Symmes Township, OH (US); Songtao Zhou, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/066,074

(22) Filed: Oct. 29, 2013

(65) Prior Publication Data

US 2014/0121268 A1   May 1, 2014

Related U.S. Application Data

(60) Provisional application No. 61/719,738, filed on Oct. 29, 2012.

(51) Int. Cl.
| | | |
|---|---|---|
| *A61K 8/42* | (2006.01) | |
| *A61K 8/44* | (2006.01) | |
| *A61Q 19/10* | (2006.01) | |
| *A61K 8/46* | (2006.01) | |
| *A61K 8/34* | (2006.01) | |

(52) U.S. Cl.
CPC ............ *A61K 8/463* (2013.01); *A61K 8/345* (2013.01); *A61K 8/44* (2013.01); *A61Q 19/10* (2013.01); *A61K 2800/30* (2013.01); *A61K 2800/596* (2013.01)

(58) Field of Classification Search
CPC . A61Q 5/02; A61Q 5/12; A61Q 19/10; A61Q 19/00; A61Q 17/04; A61Q 15/00; A61Q 11/00; A61Q 19/007; A61Q 17/005; A61Q 13/00; A61Q 19/02; A61Q 19/08; A61Q 5/006; A61Q 5/04; A61Q 9/02; A61Q 5/00
See application file for complete search history.

(56) References Cited

U.S. PATENT DOCUMENTS

| | | |
|---|---|---|
| 5,109,127 A | 4/1992 | Sekiguchi |
| 5,120,464 A | 6/1992 | Kamegai et al. |
| 5,352,386 A | 10/1994 | Rahman et al. |
| 5,352,387 A | 10/1994 | Rahman et al. |
| 5,358,656 A | 10/1994 | Humphreys et al. |
| 5,385,685 A | 1/1995 | Humphreys et al. |
| 5,393,450 A | 2/1995 | Shana'a |
| 5,447,652 A | 9/1995 | Nozaki et al. |
| 5,529,712 A | 6/1996 | Sano et al. |
| 5,529,768 A | 6/1996 | Pocalyko et al. |
| 5,632,978 A | 5/1997 | Moore et al. |
| 5,641,813 A | 6/1997 | Franklin et al. |
| 5,653,970 A | 8/1997 | Vermeer |
| 5,674,511 A | 10/1997 | Kacher et al. |
| 5,709,852 A | 1/1998 | Gopalkrishnan et al. |
| 5,716,920 A | 2/1998 | Glenn, Jr. et al. |
| 5,734,029 A | 3/1998 | Wulff et al. |
| 5,854,199 A | 12/1998 | Oshimura et al. |
| 5,854,293 A | 12/1998 | Glenn, Jr. |
| 5,858,343 A | 1/1999 | Szymczak |
| 5,858,938 A | 1/1999 | Glenn, Jr. et al. |
| 5,863,521 A | 1/1999 | Schaefer et al. |
| 5,869,070 A | 2/1999 | Dixon et al. |
| 5,880,076 A | 3/1999 | Vermeer |
| 5,905,062 A | 5/1999 | Elliott et al. |
| 5,919,748 A | 7/1999 | Noguchi et al. |
| 5,928,657 A | 7/1999 | Simon |
| 5,929,019 A | 7/1999 | Puvvada et al. |
| 5,932,528 A | 8/1999 | Glenn, Jr. et al. |
| 5,942,477 A | 8/1999 | Giret et al. |
| 5,961,992 A | 10/1999 | Ilardi et al. |
| 5,965,502 A * | 10/1999 | Balzer ......................... 510/158 |
| 5,968,491 A | 10/1999 | Richardson |
| 5,968,496 A | 10/1999 | Linares et al. |
| 5,976,520 A | 11/1999 | Babinski et al. |
| 5,994,280 A | 11/1999 | Giret et al. |
| 6,028,043 A | 2/2000 | Glenn, Jr. et al. |
| 6,033,680 A | 3/2000 | Dixon et al. |
| 6,057,275 A | 5/2000 | Fair et al. |
| 6,107,261 A | 8/2000 | Taylor et al. |
| 6,121,214 A | 9/2000 | Exner et al. |
| 6,126,954 A | 10/2000 | Tsaur |
| 6,194,364 B1 | 2/2001 | Glenn, Jr. |
| 6,277,797 B1 | 8/2001 | Glenn, Jr. et al. |
| 6,306,805 B1 | 10/2001 | Bratescu et al. |
| 6,322,799 B1 | 11/2001 | Ilardi et al. |
| 6,329,331 B1 | 12/2001 | Aronson et al. |

(Continued)

FOREIGN PATENT DOCUMENTS

| | | |
|---|---|---|
| CN | 101703454 A | 5/2010 |
| DE | 19646413 A1 | 5/1998 |
| DE | 19705862 C1 | 6/1998 |
| DE | 10007321 A1 | 8/2001 |
| EP | 353735 A2 | 2/1990 |
| EP | 409005 A2 | 1/1991 |
| EP | 473502 A1 | 3/1992 |
| EP | 485212 A1 | 5/1992 |
| EP | 493927 A1 | 7/1992 |
| EP | 530866 A1 | 3/1993 |
| EP | 531684 A1 | 3/1993 |
| EP | 559375 A1 | 9/1993 |
| EP | 560322 A1 | 9/1993 |
| EP | 0 681 832 A2 | 11/1995 |
| EP | 706791 A1 | 4/1996 |
| EP | 853941 A2 | 7/1998 |
| EP | 884380 A2 | 12/1998 |
| EP | 1352644 A1 | 10/2003 |
| EP | 1422288 A1 | 5/2004 |
| EP | 1661976 A1 | 5/2006 |
| EP | 1672054 A1 | 6/2006 |
| EP | 2042216 A1 | 4/2009 |

(Continued)

OTHER PUBLICATIONS

International Search Report and Written Opinion of the International Searching Authority mailed Feb. 5, 2014, PCT/US2013/067159, 17 pages.

(Continued)

*Primary Examiner* — Audrea Buckley

(57) ABSTRACT

A personal care composition exhibiting a tan delta of about 0.30 or more at about 10° C. includes a primary surfactant, secondary surfactant, and a polyol. Methods are also provided to improve the stability of a personal care composition.

16 Claims, No Drawings

(56) References Cited

U.S. PATENT DOCUMENTS

| | | |
|---|---|---|
| 6,329,353 B1 | 12/2001 | Dalrymple et al. |
| 6,352,689 B1 | 3/2002 | Szymczak |
| 6,358,493 B1 | 3/2002 | Birkel et al. |
| 6,387,857 B2 | 5/2002 | Chambers et al. |
| 6,395,701 B1 | 5/2002 | Connor et al. |
| 6,407,044 B2 | 6/2002 | Dixon |
| 6,432,896 B1 | 8/2002 | Inaba et al. |
| 6,444,629 B1 | 9/2002 | Elliott et al. |
| 6,475,474 B1 | 11/2002 | Ricca |
| 6,489,274 B1 | 12/2002 | LeGrow et al. |
| 6,506,713 B1 | 1/2003 | Slavtcheff et al. |
| 6,506,714 B1 | 1/2003 | Soriano et al. |
| 6,525,034 B2 | 2/2003 | Dalrymple et al. |
| 6,551,971 B2 | 4/2003 | Inaba et al. |
| 6,566,313 B1 | 5/2003 | Hohenstein et al. |
| 6,569,439 B1 | 5/2003 | Stier |
| 6,602,845 B2 | 8/2003 | Connor et al. |
| 6,624,126 B1 | 9/2003 | Kasuga et al. |
| 6,641,825 B2 | 11/2003 | Scholz et al. |
| 6,645,511 B2 | 11/2003 | Aronson et al. |
| 6,660,285 B2 | 12/2003 | Ricca |
| 6,692,754 B1 | 2/2004 | Makimoto et al. |
| 6,696,067 B2 | 2/2004 | Brandt et al. |
| 6,699,824 B1 | 3/2004 | Dawson et al. |
| 6,706,679 B1 | 3/2004 | Bergeron et al. |
| 6,716,440 B2 | 4/2004 | Aronson et al. |
| 6,797,683 B2 | 9/2004 | Shana'a et al. |
| 6,821,942 B2 | 11/2004 | Sebillotte-Arnaud et al. |
| 6,849,584 B2 | 2/2005 | Geary et al. |
| 6,855,677 B1 | 2/2005 | Matsumoto et al. |
| 6,903,057 B1 | 6/2005 | Tsaur |
| 6,905,694 B1 | 6/2005 | Modi |
| 6,906,016 B1 | 6/2005 | Tsaur |
| 6,916,777 B2 | 7/2005 | Connor et al. |
| 6,927,201 B2 | 8/2005 | Hsu et al. |
| 6,949,502 B2 | 9/2005 | Trinh et al. |
| 6,977,238 B1 | 12/2005 | Wetzel et al. |
| 7,041,627 B2 | 5/2006 | Kruse et al. |
| 7,045,491 B2 * | 5/2006 | Hourigan ............ 510/141 |
| 7,138,365 B2 | 11/2006 | Murayama |
| 7,186,674 B2 | 3/2007 | Guillou et al. |
| 7,211,273 B2 | 5/2007 | Hsu |
| 7,223,799 B2 | 5/2007 | Sakiguchi et al. |
| 7,259,131 B2 | 8/2007 | Fan et al. |
| 7,268,106 B2 | 9/2007 | Arai |
| 7,279,456 B2 | 10/2007 | Dufay et al. |
| 7,288,616 B2 | 10/2007 | Tamareselvy et al. |
| 7,297,667 B2 | 11/2007 | Potechin et al. |
| 7,297,717 B2 | 11/2007 | Iwai et al. |
| 7,318,929 B2 | 1/2008 | Schieferstein et al. |
| 7,332,467 B2 | 2/2008 | Schneiderman et al. |
| 7,354,891 B2 | 4/2008 | Arai |
| 7,455,848 B2 | 11/2008 | Hessefort et al. |
| 7,488,841 B2 | 2/2009 | Yamawaki et al. |
| 7,504,370 B2 | 3/2009 | Matsumoto et al. |
| 7,560,125 B2 | 7/2009 | Ananthapadmanabhan et al. |
| 7,566,448 B2 | 7/2009 | Becker et al. |
| 7,582,592 B2 | 9/2009 | Yamamoto et al. |
| 7,649,047 B2 | 1/2010 | Tamareselvy et al. |
| 7,655,744 B2 | 2/2010 | Miyanaga |
| 7,670,999 B2 | 3/2010 | Sebillotte-Arnaud et al. |
| 7,700,123 B2 | 4/2010 | Sawaki et al. |
| 7,704,932 B2 | 4/2010 | Evans et al. |
| 7,713,520 B2 | 5/2010 | Sakuta |
| 7,737,103 B2 | 6/2010 | Hloucha et al. |
| 7,776,318 B2 | 8/2010 | Bissey-Beugras et al. |
| 7,829,070 B2 | 11/2010 | Nguyen-Kim et al. |
| 7,858,567 B2 | 12/2010 | Yamamoto et al. |
| 7,863,479 B2 | 1/2011 | Tropsch et al. |
| 7,879,780 B2 | 2/2011 | Tsaur |
| 7,902,135 B2 | 3/2011 | Roso et al. |
| 7,915,208 B2 | 3/2011 | Roso et al. |
| 7,947,260 B2 | 5/2011 | Tobita |
| 7,981,851 B2 | 7/2011 | Luciow et al. |
| 8,071,115 B2 | 12/2011 | Sawaki et al. |
| 8,076,277 B2 | 12/2011 | Luciow et al. |
| 8,105,691 B2 | 1/2012 | Takeuchi et al. |
| 8,110,533 B1 | 2/2012 | Tsaur |
| 8,232,321 B2 | 7/2012 | Ohmori et al. |
| 8,277,786 B2 | 10/2012 | Yang et al. |
| 8,343,520 B2 | 1/2013 | Seigneurin et al. |
| 8,361,448 B2 | 1/2013 | Johnson et al. |
| 8,388,939 B2 | 3/2013 | Fournial et al. |
| 8,394,500 B2 | 3/2013 | Beumer et al. |
| 8,404,258 B2 | 3/2013 | Oguchi et al. |
| 9,463,151 B2 | 10/2016 | Souda et al. |
| 2001/0044393 A1 | 11/2001 | Peterson, Jr. et al. |
| 2001/0056049 A1 | 12/2001 | Aronson et al. |
| 2002/0006882 A1 | 1/2002 | Loffler et al. |
| 2002/0006883 A1 | 1/2002 | Dixon |
| 2002/0010109 A1 | 1/2002 | Chambers et al. |
| 2002/0010113 A1 | 1/2002 | Kilpatrick-Liverman et al. |
| 2002/0051819 A1 | 5/2002 | Kuhner et al. |
| 2002/0072483 A1 | 6/2002 | Barresi et al. |
| 2002/0193266 A1 | 12/2002 | Matsumoto et al. |
| 2003/0003069 A1 | 1/2003 | Carson et al. |
| 2003/0064042 A1 | 4/2003 | Bergquist et al. |
| 2003/0086892 A1 | 5/2003 | Klug et al. |
| 2003/0100457 A1 | 5/2003 | Ariotto et al. |
| 2003/0175232 A1 | 9/2003 | Elliott et al. |
| 2003/0211057 A1 | 11/2003 | Majeti et al. |
| 2003/0236180 A1 | 12/2003 | Connor et al. |
| 2004/0028711 A1 | 2/2004 | Uchida et al. |
| 2004/0033913 A1 | 2/2004 | Dahms et al. |
| 2004/0042986 A1 | 3/2004 | Meyer et al. |
| 2004/0043045 A1 | 3/2004 | Seipel et al. |
| 2004/0048758 A1 | 3/2004 | Zhang et al. |
| 2004/0052754 A1 | 3/2004 | West et al. |
| 2004/0076654 A1 | 4/2004 | Vinson et al. |
| 2004/0097472 A1 | 5/2004 | West et al. |
| 2004/0115230 A1 | 6/2004 | Divone et al. |
| 2004/0116539 A1 | 6/2004 | Biercevicz et al. |
| 2004/0146540 A1 | 7/2004 | Ueda et al. |
| 2004/0161482 A1 | 8/2004 | Kawada et al. |
| 2004/0197361 A1 | 10/2004 | Oguchi et al. |
| 2004/0219125 A1 | 11/2004 | Yoneda et al. |
| 2004/0234484 A1 | 11/2004 | Peffly et al. |
| 2004/0235702 A1 | 11/2004 | Hawkins |
| 2004/0241124 A1 | 12/2004 | Lannibois-Drean et al. |
| 2004/0266656 A1 | 12/2004 | Sakurai |
| 2005/0008601 A1 | 1/2005 | Ariotto et al. |
| 2005/0042261 A1 | 2/2005 | Hasenoehrl et al. |
| 2005/0096249 A1 | 5/2005 | Jonas et al. |
| 2005/0153869 A1 | 7/2005 | Connor et al. |
| 2005/0154180 A1 | 7/2005 | Hessefort et al. |
| 2005/0192189 A1 | 9/2005 | Wagner et al. |
| 2005/0201965 A1 | 9/2005 | Kuhlman et al. |
| 2005/0227902 A1 | 10/2005 | Erazo-Majewicz et al. |
| 2005/0256313 A1 | 11/2005 | Norenberg et al. |
| 2005/0276829 A1 | 12/2005 | Stella et al. |
| 2005/0277568 A1 | 12/2005 | Keenan et al. |
| 2005/0296950 | 12/2005 | Chrisstoffels et al. |
| 2006/0009368 A1 | 1/2006 | Norenberg et al. |
| 2006/0019847 A1 | 1/2006 | Fan et al. |
| 2006/0051430 A1 | 3/2006 | Arata et al. |
| 2006/0062751 A1 | 3/2006 | Sato et al. |
| 2006/0073110 A1 | 4/2006 | Modi |
| 2006/0079418 A1 | 4/2006 | Wagner et al. |
| 2006/0079420 A1 | 4/2006 | Wagner et al. |
| 2006/0083761 A1 | 4/2006 | Yoshimi et al. |
| 2006/0088495 A1 | 4/2006 | Harichian et al. |
| 2006/0089286 A1 | 4/2006 | Chakrabarty et al. |
| 2006/0093689 A1 | 5/2006 | Kawada et al. |
| 2006/0100115 A1 | 5/2006 | Sakurai et al. |
| 2006/0115440 A1 | 6/2006 | Arata et al. |
| 2006/0116305 A1 | 6/2006 | Yamato et al. |
| 2006/0122322 A1 | 6/2006 | Chrisstoffels et al. |
| 2006/0134045 A1 | 6/2006 | Cao et al. |
| 2006/0134047 A1 | 6/2006 | Bakeev et al. |
| 2006/0142174 A1 | 6/2006 | Fukuda et al. |
| 2006/0160713 A1 | 7/2006 | Sekine et al. |
| 2006/0165639 A1 | 7/2006 | Gauweiler et al. |
| 2006/0183662 A1 | 8/2006 | Crotty et al. |
| 2006/0189495 A1 | 8/2006 | LiBrizzi et al. |

(56) References Cited

U.S. PATENT DOCUMENTS

| | | |
|---|---|---|
| 2006/0228319 A1 | 10/2006 | Vona, Jr. et al. |
| 2007/0027050 A1 | 2/2007 | Crotty et al. |
| 2007/0081953 A1 | 4/2007 | Dahms |
| 2007/0105746 A1 | 5/2007 | Dahms |
| 2007/0134176 A1 | 6/2007 | Fukui et al. |
| 2007/0172441 A1 | 7/2007 | Takeda et al. |
| 2007/0202071 A1 | 8/2007 | Morvan et al. |
| 2007/0212320 A1 | 9/2007 | Demitz et al. |
| 2007/0213243 A1 | 9/2007 | Yao et al. |
| 2007/0243144 A1 | 10/2007 | Takagaki |
| 2007/0243241 A1 | 10/2007 | Lin et al. |
| 2007/0264204 A1 | 11/2007 | Noor et al. |
| 2007/0274942 A1 | 11/2007 | Morvan et al. |
| 2007/0286832 A1 | 12/2007 | Clapp et al. |
| 2008/0031842 A1 | 2/2008 | Kuhlman et al. |
| 2008/0031845 A1 | 2/2008 | Stella et al. |
| 2008/0075684 A1 | 3/2008 | Barg et al. |
| 2008/0108535 A1 | 5/2008 | Aubrun-Sonneville |
| 2008/0124295 A1 | 5/2008 | Duranton et al. |
| 2008/0169215 A1 | 7/2008 | Tanaka et al. |
| 2008/0171794 A1 | 7/2008 | Yamamoto et al. |
| 2008/0193404 A1 | 8/2008 | Lange et al. |
| 2008/0214776 A1 | 9/2008 | Llosas et al. |
| 2008/0214850 A1 | 9/2008 | Llosas et al. |
| 2008/0233061 A1 | 9/2008 | Gates et al. |
| 2008/0234172 A1 | 9/2008 | McGee et al. |
| 2008/0255015 A1 | 10/2008 | Beilfuss et al. |
| 2008/0299054 A1 | 12/2008 | Chandar et al. |
| 2009/0062406 A1 | 3/2009 | Loffler |
| 2009/0069522 A1 | 3/2009 | Hessefort et al. |
| 2009/0081137 A1 | 3/2009 | Nguyen Kim et al. |
| 2009/0093388 A1 | 4/2009 | Yamawaki et al. |
| 2009/0197791 A1 | 8/2009 | Balastre et al. |
| 2009/0214608 A1 | 8/2009 | Monin et al. |
| 2009/0238769 A1 | 9/2009 | Joziak et al. |
| 2009/0239776 A1 | 9/2009 | Myers |
| 2009/0280071 A1 | 11/2009 | Kumar et al. |
| 2009/0297462 A1 | 12/2009 | Hessefort et al. |
| 2009/0305929 A1 | 12/2009 | Luciow et al. |
| 2010/0008884 A1 | 1/2010 | Brandt et al. |
| 2010/0047300 A1 | 2/2010 | Kaupp et al. |
| 2010/0061956 A1 | 3/2010 | Seigneurin et al. |
| 2010/0062961 A1 | 3/2010 | Post et al. |
| 2010/0075881 A1 | 3/2010 | Tsaur |
| 2010/0075882 A1 | 3/2010 | Ohmori et al. |
| 2010/0098646 A1 | 4/2010 | Carnali et al. |
| 2010/0120645 A1 | 5/2010 | Fares et al. |
| 2010/0197543 A1 | 8/2010 | Yamato et al. |
| 2010/0222305 A1 | 9/2010 | West et al. |
| 2010/0234260 A1 | 9/2010 | Sekine et al. |
| 2010/0254928 A1 | 10/2010 | Yamazaki et al. |
| 2010/0256031 A1 | 10/2010 | Wu et al. |
| 2010/0261670 A1 | 10/2010 | West et al. |
| 2010/0311628 A1 | 12/2010 | Librizzi et al. |
| 2010/0317555 A1 | 12/2010 | Araki et al. |
| 2011/0033398 A1 | 2/2011 | Cauvin et al. |
| 2011/0082105 A1 | 4/2011 | Fevola et al. |
| 2011/0110874 A1 | 5/2011 | Tanaka et al. |
| 2011/0150818 A1 | 6/2011 | Canfield et al. |
| 2011/0152150 A1 | 6/2011 | Bernard |
| 2011/0155165 A1 | 6/2011 | Yamato et al. |
| 2011/0230380 A1 | 9/2011 | Holzhauer et al. |
| 2012/0003338 A1 | 1/2012 | Myers |
| 2012/0009127 A1 | 1/2012 | Dasgupta et al. |
| 2012/0009285 A1 | 1/2012 | Wei et al. |
| 2012/0014885 A1 | 1/2012 | Collier et al. |
| 2012/0046210 A1 | 2/2012 | Patel et al. |
| 2012/0070399 A1 | 3/2012 | Jegou |
| 2012/0071568 A1 | 3/2012 | Sugiyama et al. |
| 2012/0077880 A1 | 3/2012 | Quan et al. |
| 2012/0077881 A1 | 3/2012 | Quan et al. |
| 2012/0101172 A1 | 4/2012 | Beutler et al. |
| 2012/0114573 A1 | 5/2012 | Amalric et al. |
| 2012/0145171 A1 | 6/2012 | Ananthapadmanabhan et al. |
| 2012/0183590 A1 | 7/2012 | Seigneurin et al. |
| 2012/0183591 A1 | 7/2012 | Dahms |
| 2012/0322712 A1 | 12/2012 | Yao et al. |

FOREIGN PATENT DOCUMENTS

| | | |
|---|---|---|
| EP | 2455063 A1 | 5/2012 |
| FR | 2843971 A1 | 5/2004 |
| GB | 2290551 A | 1/1996 |
| GB | 2297761 A | 8/1996 |
| GB | 2297975 A | 8/1996 |
| JP | 05208905 A | 8/1993 |
| JP | 06016523 A | 1/1994 |
| JP | 08020525 A | 1/1996 |
| JP | 2000290148 A | 10/2000 |
| JP | 2001139456 A1 | 5/2001 |
| JP | 2001140000 A | 5/2001 |
| JP | 2002265990 A | 9/2002 |
| JP | 2004155716 A1 | 6/2004 |
| JP | 2005015359 A | 1/2005 |
| JP | 2006028278 A | 2/2006 |
| JP | 2006249124 A | 9/2006 |
| JP | 2006299163 A | 11/2006 |
| JP | 2009221121 A | 10/2009 |
| JP | 5183859 B2 | 4/2013 |
| KR | 2008035821 A | 4/2008 |
| WO | WO9205240 A1 | 4/1992 |
| WO | WO9417783 A2 | 8/1994 |
| WO | WO9418292 A1 | 8/1994 |
| WO | WO9423695 A1 | 10/1994 |
| WO | WO9513355 A1 | 5/1995 |
| WO | WO9603974 A1 | 2/1996 |
| WO | WO9827938 A1 | 7/1998 |
| WO | WO9924546 A1 | 5/1999 |
| WO | WO9938489 A1 | 8/1999 |
| WO | WO9938490 A1 | 8/1999 |
| WO | WO9938491 A1 | 8/1999 |
| WO | WO0015180 A1 | 3/2000 |
| WO | WO0115659 A2 | 3/2001 |
| WO | WO0126620 A1 | 4/2001 |
| WO | WO0172262 A2 | 10/2001 |
| WO | WO03084501 A1 | 10/2003 |
| WO | WO2004004678 A1 | 1/2004 |
| WO | WO2004035012 A1 | 4/2004 |
| WO | WO2004064802 A2 | 8/2004 |
| WO | WO2005049782 A1 | 6/2005 |
| WO | WO2006083843 A1 | 8/2006 |
| WO | WO2009103576 A1 | 8/2009 |
| WO | WO2012078159 A1 | 6/2012 |
| WO | WO2012086847 A2 | 6/2012 |

OTHER PUBLICATIONS

Compositions with Beneficial Properties for Consumers, Ip.Com Journal, Oct. 21, 2008, 35 pages.
Disinfectant Concentrates as Additives in Various Compositions and Uses, IP.com Journal, Mar. 20, 2008, 68 pages.

* cited by examiner

PERSONAL CARE COMPOSITIONS

TECHNICAL FIELD

The present disclosure generally relates to personal care compositions comprising polyols and methods related thereto.

BACKGROUND

The desirability of personal care compositions can be influenced by a variety of factors. For example, consumers are likely to desire personal care compositions that exhibit suitable cleaning and lathering characteristics, are non-drying to the skin, and display favorable rheological properties. Additionally, other factors such as environmental temperature can affect the desirability of the personal care composition as fluctuations in temperature can affect the viscosity and/or elasticity of the personal care composition; potentially impacting the consumer's opinion of whether the personal care composition displays favorable rheological properties. Balancing these qualities can be challenging as the choice of surfactant(s) and other substances in the personal composition can affect one or more or more of these factors. Thus, there is a need in the market for personal care compositions that exhibit suitable cleaning and lathering characteristics, are non-drying to the skin, and display favorable rheological properties.

SUMMARY

A personal care composition comprising a primary surfactant, a secondary surfactant, and a polyol. The primary surfactant comprises an anionic surfactant not sodium lauryl sulfate or ammonium lauryl sulfate. The secondary surfactant comprises a zwitterionic surfactant, an amphoteric surfactant, a non-ionic surfactant, or a combination thereof. The personal care composition exhibits a tan delta of about 0.30 or more at about 10° C.

A personal care composition comprising: a primary surfactant comprising sodium laureth (3) sulfate; a secondary surfactant comprising a zwitterionic surfactant, an amphoteric surfactant, a non-ionic surfactant, or a combination thereof; a viscosity modifier; and sorbitol comprising from about 0.5% to less than 10% by weight of the personal care composition; wherein the personal care composition exhibits a tan delta of about 0.35 or more at about 10° C. and is substantially free of sodium lauryl sulfate.

DETAILED DESCRIPTION

This application claims priority to U.S. provisional application No. 61/719,738 filed Oct. 29, 2012, which is incorporated herein by reference.

While the specification concludes with the claims particularly pointing and distinctly claiming the invention, it is believed that the present invention will be better understood from the following description.

The devices, apparatuses, methods, components, and/or compositions of the present invention can include, consist essentially of, or consist of, the components of the present invention as well as other ingredients described herein.

All percentages and ratios used herein are by weight of the total personal care composition and all measurements made are at 25° C., unless otherwise designated.

All measurements used herein are in metric units unless otherwise specified.

DEFINITIONS

"ALS" refers to ammonium lauryl sulfate.
"CAPB" refers to cocamidopropyl betaine.
"SLS" refers to sodium lauryl sulfate.
"SLES" refers to sodium laureth(n) sulfate.

The term "personal care composition" as used herein, refers to compositions intended for topical application to the skin and/or hair.

The phrase "substantially free of" as used herein, unless otherwise specified means that the personal care composition comprises less than about 2%, less than about 1%, and less than about 0.1% of the stated ingredient. The term "free of" as used herein means that the personal care composition comprise 0% of the stated ingredient that is, the ingredient has not been added to the personal care composition. However, these ingredients may incidentally form as a byproduct or a reaction product of the other components of the personal care composition.

"Stable" refers to a personal care composition having a tan delta greater than about 0.30, about 0.31, about 0.32, about 0.33, about 0.34, or about 0.35 at 10° C. as measured by the method described herein, unless otherwise stated.

Personal Care Compositions

The personal care compositions can be rinse-off formulations that can be applied topically to the skin and/or hair and rinsed from the skin and/or hair within minutes with water. The personal care compositions can exhibit a viscosity of from about 1,000 centipoise (cP) to about 1,000,000 cP, about 1,500 centipoise (cP) to about 1,000,000 cP, from about 5,000 centipoise (cP) to about 1,000,000 cP, from about 6,000 centipoise (cP) to about 1,000,000 cP, or from about 8,000 centipoise (cP) to about 1,000,000 cP, at about 25° C. as measured by the method described herein. The personal care compositions can also be used as shaving aids. The personal care compositions can be extrudable or dispensable from a package. The personal care compositions can be in the form of, for example, a liquid, semi-liquid cream, lotion, or gel and can be intended for topical application to the skin and/or hair. Examples of personal care compositions can include, but are not limited to, shampoo, conditioning shampoo, body wash, moisturizing body wash, shower gels, skin cleansers, cleansing milks, hair and body wash, in shower body moisturizer, pet shampoo, shaving preparations, and cleansing compositions used in conjunction with a disposable cleansing cloth.

The desirability of personal care compositions can be influenced by a variety of factors including the amount and types of surfactants present in the personal care composition. Many consumers use personal care compositions because the personal care compositions can remove dirt, sweat, sebum, and other substances from the skin and/or hair. However, in addition to the cleaning properties displayed by the personal care composition, the desirability of the personal care composition can be also influenced by other factors.

For example, the desirability of a personal care composition can vary depending on the type and amount of the surfactants included in a formulation of a personal care composition. In this regard, a consumer may view a personal care composition as unfavorable when the personal care composition includes surfactants that promote the drying of the skin. Additionally, because many consumers equate cleaning efficiency with the level of foam generated upon using a particular personal care composition, consumers may not desire personal care compositions that include surfactants that do not foam to the level desired. Also potentially impacting the consumers' perception of a personal care composition are the rheological properties displayed by the personal care composition. For example, temperature fluctuations may cause changes in the rheological properties of the personal care composition such that the consumer perceives the product as being too thick and/or indispensable. The balancing of the aforementioned factors while concurrently maintaining the cleaning properties of the personal care composition can be a challenging endeavor.

In addition to the above complexities, some consumers desire a thick product. Thick products can be created by increasing the viscosity of a personal care composition. However, viscosity can be linked to the elastic behavior of the personal care composition, so increasing the viscosity can have negative effects on product feel. One such negative effect is the development of a springy or gel-like character which consumers can dislike.

The rheological behavior of a personal care composition can be characterized by its tan delta. Increasing the viscosity of a personal care composition can lower its tan delta to an unacceptable level, giving the personal care composition an undesired gel-like consistency. Thus, a personal care composition's viscosity and tan delta can be balanced to give the consumer a more acceptable product. For example, a personal care composition with a tan delta above about 0.30, above about 0.31, above about 0.32, above about 0.33, above about 0.34, or above about 0.35 at 10° C. may be perceived by a consumer as having sufficient viscosity to flow over the skin, but not too gel-like or otherwise difficult to spread on the skin or dispense from the package. In contrast, a personal care composition with a tan delta below about 0.30 at 10° C. may be perceived as too gel-like and difficult to spread on the skin and dispense from the container. Additionally, a personal care composition with a thickness below 5000 cP at about 25° C. may be perceived as too thin. In contrast, a personal care composition with a thickness above 5000 cP at about 25° C. may be perceived as having sufficient thickness. The personal care compositions can have a tan delta up to about 20.

A personal care composition's tan delta can fluctuate not only with changes in viscosity, but also across temperature. For example, although a personal care composition may have an acceptable tan delta at room temperature (e.g., 25° C.), the tan delta may be too low at lower temperatures such as at about 10° C. In order to have a composition that can be shipped, stored, and used in all seasons, a tan delta of about 0.30 or more measured at about 10° C. is desired.

It has presently been discovered that the inclusion of certain types of surfactants, like sodium lauryl sulfate (SLS) and other non-ethoxylated alkyl sulfates, can negatively affect the tan delta of a personal care composition at low temperature. Without being limited by theory, this is believed to be due, at least in part, to the degree to which the micelles formed by the surfactant in a personal care composition can compact. SLS is a smaller surfactant molecule and tends to allow for more rigid packing of the micelles. It is believed this more rigid packing can lead to instability of the composition at low temperatures resulting in a lower tan delta. Thus, the stability of a personal care composition at low temperatures can be increased by the removal of SLS from a personal care composition.

Surprisingly, it has also been found that the addition of particular polyols to certain personal care compositions that are free, or substantially free, of SLS can enhance the viscosity and/or improve the rheological properties of certain personal care composition. Surprisingly, it has also been found that even levels of polyols less than about 10% or less by weight of the personal care composition can enhance the viscosity and/or improve the rheological properties of certain personal care compositions free or substantially free of non-ethoxylated alkyl sulfates.

The finding that the addition of particular polyols to certain personal care compositions that are free or substantially free of non-ethoxylated alkyl sulfates can enhance the viscosity and/or improve the rheological properties of the personal care composition is surprising, for example, given the unpredictable nature of polyols in personal care compositions. In this regard, the inclusion of high levels of polyols like glycerin in certain personal care compositions containing sulfosuccinic acid monoester surfactants has been shown to potentially lead to the destabilization of certain personal care compositions.

Primary Surfactants

The personal care composition can comprise a primary surfactant that can comprise an anionic surfactant. The primary surfactant can comprise from about 5% to about 10%, from about 6.4% to about 10%, and from about 6.4% to about 8.4% by weight of the personal care composition. The anionic surfactant can be sodium laureth(n) sulfate, hereinafter SLEnS, wherein n defines the average moles of ethoxylation. The anionic surfactant can also be ammonium laureth(n) sulfate, hereinafter ALEnS, wherein n defines the average moles of ethoxylation. For example, n can range from greater than about 0 to about 3, alternatively from about 0.5 to about 2.7, alternatively from about 1.1 to about 2.5, alternatively from greater than about 0 to about 2.5, alternatively from about 1.8 to about 2.2, or alternatively about 2. It is understood that a material such as SLE3S, for example, may comprise a significant amount of molecules which have no ethoxylate, 1 mole ethoxylate, 4 mole ethoxylate, and so on in a distribution which can be broad, narrow or truncated, while still comprising SLE3S wherein the average of the distribution is about 3. It is understood that a material such as SLE2S, for example, may comprise a significant amount of molecules which have no ethoxylate, 1 mole ethoxylate, 4 mole ethoxylate, and so on in a distribution which can be broad, narrow or truncated, while still comprising SLE2S wherein the average of the distribution is about 2. It is understood that a material such as SLE1S, for example, may comprise a significant amount of molecules which have no ethoxylate, 1 mole ethoxylate, 4 mole ethoxylate, and so on in a distribution which can be broad, narrow or truncated, while still comprising SLE2S wherein the average of the distribution is about 1.

The anionic surfactant can also be sodium trideceth(n) sulfate (hereinafter STnS) and/or ammonium trideceth(n) sulfate (hereinafter ATnS), wherein n defines the average moles of ethoxylation. For example, n can range from greater than 0 to 3, alternatively from 0.5 to 2.7, alternatively from 1.1 to 2.5, alternatively from greater than 0 to 2.5, alternatively from 1.8 to 2.2, alternatively about 2. It is understood that a material such as ST2S, for example, may comprise a significant amount of molecules which have no ethoxylate, 1 mole ethoxylate, 3 mole ethoxylate, and so on in a distribution which can be broad, narrow or truncated, while still comprising ST2S wherein the average of the distribution is about 2.

Other anionic surfactants suitable for use in the personal cleansing compositions are the succinates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other examples of anionic surfactants for use in the personal cleansing compositions include sodium lauryl sarcosinate, sodium lauroyl sarcosinate, lauryl sarcosine, cocoyl sarcosine, alkyl phosphate esters, ethoxylated alkyl phosphate esters, and combinations thereof.

Often, SLE1S, SLE2S, and SLE3S are combined with SLS in personal care compositions. Examples of personal care compositions can comprise less than about 2% SLS, alternatively less than about 1% SLS, alternatively less than about 0.5% SLS, alternatively less than about 0.1% SLS, alternatively less than about 0.05% SLS, alternatively between about 0.01% SLS and about 0.05% SLS, alternatively about 0% SLS.

Often, SLE1S, SLE2S, and SLE3S or ALE1S, ALE2S, and ALE3S are combined with ALS in personal care compositions. Examples of personal care compositions can comprise less than about 2% ALS, alternatively less than about 1% ALS, alternatively less than about 0.5% ALS, alternatively less than about 0.1% ALS, alternatively less than about 0.05% ALS, alternatively between about 0.01% ALS and about 0.05% ALS, alternatively about 0% ALS.

Cosurfactants

The personal care compositions can also comprise a cosurfactant. Cosurfactants can comprise from 0.1% to 20%, from about 2% to about 10%, or from about 2% to about 5% by weight of the personal care composition. Cosurfactants may also comprise more than 20% by weight of the personal care composition. Cosurfactants can comprise amphoteric surfactants, zwitterionic surfactants, non-ionic surfactants, and mixtures thereof.

Examples of amphoteric/zwitterionic surfactants are betaine surfactants. Examples of betaine surfactants useful herein include the high alkyl betaines such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxyethyl) carboxy methyl betaine, stearyl bis-(2-hydroxy-propyl) carboxymethyl betaine, oleyl dimethyl gamma-carboxypropyl betaine, lauryl bis-(2-hydroxypropyl) alpha-carboxyethyl betaine, etc. Other betaines are the sulfobetaines which may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amido betaines and amidosulfobetaines, wherein an $RCONH(CH_2)_x$ radical is attached to the nitrogen atoms of the betaine are also useful in this invention. A preferred betaine is cocamidopropyl betaine.

Other useful surfactants include the amphoacetates such as sodium laurylamphoacetate and nonionic surfactants like, for example, glucosides such as decyl glucosides, monoglycerides such as glyceryl monolaurate, alkanolamides such as cocomonoethanolamide, and glyceryl ethers such as PEG-80 glyceryl cocoate.

Water

The liquid personal cleansing compositions of the present invention can also contain from about 20% to about 95%, from about 40% to about 90%, from about 60% to about 90%, and from about 70% to about 90% water by weight of the compositions.

Modifiers

The personal care compositions can further comprise a viscosity modifier for modifying the viscosity of the personal care composition. Such concentrations can range, for example, from about 0.1% to about 10%, from about 0.3% to about 5.0%, or from 0.5% to 3% by weight of the personal care compositions.

Non limiting examples of viscosity modifiers useful herein include inorganic salts. Examples of inorganic salts useful herein magnesium nitrate, trimagnesium phosphate, calcium chloride, sodium carbonate, sodium chloride, sodium aluminum sulfate, disodium phosphate, sodium polymetaphosphate, sodium magnesium succinate, sodium sulfate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, ammonium sulfate, calcium acetate, calcium nitrate, calcium phosphate, calcium sulfate, ferric sulfate, magnesium chloride, magnesium sulfate, alkyl ether sulfate, mixtures thereof, and the like.

Viscosity modifiers can also include polymers. Non limiting examples of polymers include cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carrageenan, pectin, agar, quince seed (*Cydonia oblonga* Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate, alginic acid propylene glycol esters, acrylate polymers such as sodium polyacrylate, polyethylacrylate, polyacrylamide, polyethyleneimine, and inorganic water soluble material such as bentonite, aluminum magnesium silicate, laponite, hectonite, and anhydrous silicic acid.

Polyol

The personal care compositions can further comprise polyols. Such concentrations can range, for example, from about 0.1% to about 10%, from about 0.3% to about 5.0%, or from 0.5% to 3% by weight of the personal care compositions.

Non limiting examples of polyols useful herein include glycerin, sorbitol, propylene glycol, butylene glycol, hexylene glycol, ethoxylated glucose, 1,2-hexane diol, hexanetriol, dipropylene glycol, trehalose, diglycerin, maltitol, maltose, glucose, fructose, sodium chondroitin sulfate, sodium hyaluronate, sodium adenosin phosphate, sodium lactate, pyrrolidone carbonate, glucosamine, cyclodextrin, and mixtures thereof.

Other Optional Ingredients

The personal care compositions can also include other personal care adjunct ingredients that may modify the physical, chemical, cosmetic or aesthetic characteristics of the compositions or serve as "active" components when deposited on the skin. Non limiting examples of such adjunct ingredients include preservatives (e.g., propyl paraben), deodorants, antimicrobials, fragrances, deodorant perfumes, coloring agents or dyes, thickeners, sensates, sunscreens, surfactants or emulsifiers, gellants or other suspending agents, pH modifiers, co-solvents or other additional solvents, emollients, pharmaceutical actives, vitamins, and combinations thereof. Other non-limiting examples of adjunct ingredients include: enzymes, abrasives, skin exfoliating agents, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents (e.g., resorcinol, sulfur, salicylic acid, erythromycin, zinc, etc.), anti-caking agents, antifoaming agents, additional antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), humectants, opacifying agents, pH adjusters, propellants, reducing agents, sequestrants, skin bleaching agents (or lightening agents) (e.g., hydroquinone, kojic acid, ascorbic acid, magnesium ascorbyl phosphate, ascorbyl glucosamine), skin-conditioning agents (humectants, including miscellaneous and occlusive), skin soothing and/or healing agents (e.g., panthenol and derivatives (e.g., ethyl panthenol), *aloe vera*, pantothenic acid and its derivatives, allantoin, bisabolol, and dipotassium glycyrrhizinate), skin treating agents, including agents for preventing, retarding, arresting, and/or reversing skin wrinkles (e.g., alpha-hydroxy acids such as lactic acid and glycolic acid and beta-hydroxy acids such as salicylic acid), thickeners, hydrocolloids, particular zeolites, and vitamins and derivatives thereof (e.g. tocopherol, tocopherol acetate, beta carotene, retinoic acid, retinol, retinoids, retinyl palmitate, niacin, niacinamide, panthenol, and the like).

Test Methods

The viscosity of the personal care composition can be measured using a digital Brookfield Viscometer (model RVDVII) with a CPE-41 spindle with temperature control. The viscosity is measured at 25° C., with a 1 mm gap (distance between the rotating spindle and the wall of the RVDVII), at a shear rate of 1 RPM (rotations per minute). Each measurement is taken for a period of two minutes to allow for the collection of enough data points to determine the average viscosity of the product (i.e. the spindle rotates at 1 rpm for 2 minutes).

The ratio of G" to G' (i.e. G"÷G') is referred to as the tan delta. To measure the viscous modulus (G") and elastic modulus (G') of a personal care composition, an Advanced Rheometer, AR G2 Rheometer (TA Instruments, Del., USA) equipped with a 1 degree cone upper geometry having a diameter of 40 mm and a flat plate lower geometry equipped with a peltier heating/cooling mechanism to control temperature is used. Measurements are conducted by placing approximately 1 gram of the personal care composition onto the lower test geometry and lowering the upper geometry to the desired gap of about 27 micrometers, wiping away any excess of the personal care composition to create an even surface around the edges of the upper and lower geometries. The test is conducted over a frequency range of 0.01 to 100 radians per second, collecting 10 data points per decade, using a constant oscillatory stress of 0.1 Pa and a set temperature of 10° C. or 25° C.

EXAMPLES

Comparative Examples C-1 through C-16 and Inventive Examples I-1 through I-15 were prepared by the following method. First, all of the ingredients except for NaCl are mixed for each respective personal care composition using a Speed Mixer (Model No. DAC 400 FVZ by Hauschild) for one minute at 2000 rpm. The one minute interval should be sufficient to achieve a homogenous solution. Next, the solution containing NaCl is added and all ingredients are then remixed. The viscosity and tan delta were then measured for each example as described herein.

The compositions in Tables 1 and 2 depict the percentage of each ingredient, or solution, by weight of the personal care composition. Quantities are expressed as a percentage of the ingredient added including any inactive components contained in the ingredient. As an illustrative example only, a composition containing about 25% of the sodium laureth-3 sulfate ingredient by weight of the composition, indicates a composition containing about 7.0% active sodium laureth-3 sulfate by weight of the composition (25% ingredient by weight of the composition*28% active component of the ingredient=7.0% active sodium laureth-3 sulfate by weight of the composition).

TABLE 1

| | Comparative Examples | | | | | | | | | | | | | | | |
|---|---|---|---|---|---|---|---|---|---|---|---|---|---|---|---|---|
| Ingredient | C-1 | C-2 | C-3 | C-4 | C-5 | C-6 | C-7 | C-8 | C-9 | C-10 | C-11 | C-12 | C-13 | C-14 | C-15 | C-16 |
| Water | Q.S. | Q.S. | Q.S. | Q.S. | Q.S. | Q.S. | Q.S. | Q.S. | Q.S. | Q.S. | Q.S. | Q.S. | Q.S. | Q.S. | Q.S. | Q.S. |
| SLE3S (28% active) | 23 | 30 | 23 | 23 | 28 | 23 | 30 | 30 | 30 | 23 | 23 | 23 | 23 | 28 | 23 | 22 |
| CAPB (30% active) | 3 | 12 | 3 | 3 | 4 | 3 | — | — | — | 3 | 3 | 3 | 3 | 4 | 3 | 3 |
| SLS (29% active) | 9 | — | 9 | 9 | 10 | 9 | — | — | — | 9 | 9 | 9 | 9 | 10 | 9 | 8 |
| Sorbitol (70% active) | 4.3 | — | — | 4.3 | 4.3 | 4.3 | — | — | — | 0 | 1.5 | 3 | 2 | 0 | 0 | 0 |
| Glycerin | — | — | — | — | 0.5 | — | — | — | — | — | — | — | — | — | — | — |
| Thixcin | 0.5 | — | — | 0.5 | 0.25 | — | — | — | — | — | — | — | — | — | — | — |
| Sodium Benzoate | 0.25 | 0.25 | 0.25 | 0.25 | 0.25 | 0.25 | 0.25 | 0.25 | 0.25 | 0.25 | 0.25 | 0.25 | 0.25 | 0.25 | 0.25 | 0.25 |
| Methyl-chloroisothiazolinone/methylisothiaxolinone | 0.033 | 0.033 | 0.033 | 0.033 | 0.033 | 0.033 | 0.033 | 0.033 | 0.033 | 0.033 | 0.033 | 0.033 | 0.033 | 0.033 | 0.033 | 0.033 |
| Fragrance | 1 | 1.1 | 1 | 1 | 1 | 1 | 1 | 1 | 1 | 1 | 1 | 1 | 1 | 1 | 1 | 1 |
| Na EDTA | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| HC Base (20% EDGS) | 5 | — | — | 5 | — | — | — | — | — | — | — | — | — | — | — | — |
| Euperlan (15% EDGS) | — | — | — | — | — | 0.5 | — | — | — | — | — | — | — | — | — | — |
| Polyquat-10 | 0.1 | — | — | 0.1 | — | — | — | — | — | — | — | — | — | — | — | — |
| JR 400 | — | — | — | — | — | — | — | — | — | — | — | — | — | — | — | — |
| Beads | 0.2 | — | — | 0.2 | 0.1 | — | — | — | — | — | — | — | — | — | — | — |
| Citric Acid | 0.15 | 0.15 | 0.15 | 0.15 | 0.15 | 0.15 | 0.15 | 0.15 | 0.15 | 0.15 | 0.15 | 0.15 | 0.15 | 0.15 | 0.15 | 0.15 |
| NaCl (20% active) | 10 | 5 | 5 | 10 | 9.5 | 12.5 | 10 | 10 | 10 | 10 | 10 | 10 | 10 | 10 | 10 | 10 |
| Skin Actives | 0.01 | 0.02 | 0.01 | 0.01 | 0.01 | 0.01 | — | — | — | — | — | — | — | — | — | — |
| Dyes | — | — | 0.02 | — | — | 0.02 | — | — | — | — | — | — | — | — | — | — |
| Styrene-Acrylates | — | 0.75 | — | — | — | — | — | — | — | — | — | — | — | — | — | — |
| Minerals | — | 0.02 | — | — | 0.1 | — | — | — | — | — | — | — | — | — | — | — |
| Product Viscosity (cP) | 7,552 | 5,428 | 5,256 | 7,550 | 7,300 | 10,000 | 6,500 | 7,000 | 6,250 | 7,500 | 8,000 | 8,000 | 8,900 | 5,700 | 6,200 | 6,000 |
| Product Tan Delta (25° C.) | 0.49 | 0.40 | 0.57 | 0.49 | 0.54 | 0.33 | 0.47 | 0.46 | 0.45 | 0.49 | 0.41 | 0.40 | 0.34 | 0.50 | 0.45 | 0.39 |
| Product Tan Delta (10° C.) | 0.23 | 0.30 | 0.20 | 0.23 | 0.25 | 0.08 | 0.18 | 0.17 | 0.24 | 0.23 | 0.17 | 0.21 | 0.19 | 0.25 | 0.17 | 0.14 |

TABLE 2

| Ingredient | Inventive Examples | | | | | | | |
|---|---|---|---|---|---|---|---|---|
| | I-1 | I-2 | I-3 | I-4 | I-5 | I-6 | I-7 | I-8 |
| Water | Q.S. | Q.S. | Q.S. | Q.S. | Q.S. | Q.S. | Q.S. | Q.S. |
| SLE3S (28% active) | 25 | 30 | 25 | 25 | 25 | 25 | 30 | 30 |
| CAPB (30% active) | 10 | 12 | 10 | 10 | 10 | 10 | 12 | 12 |
| SLS (29% active) | — | — | — | — | — | — | — | — |
| Sorbitol (70% active) | 4.3 | 4.3 | 8 | 8 | 4.3 | 4.3 | — | — |
| Glycerin | — | — | — | — | — | — | 1 | 2 |
| Thixcin | — | — | — | — | — | — | — | — |
| Sodium Benzoate | 0.25 | 0.25 | 0.25 | 0.25 | 0.25 | 0.25 | 0.25 | 0.25 |
| Methylchloroisothiazolinone/methylisothiaxolinone | 0.033 | 0.033 | 0.033 | 0.033 | 0.033 | 0.033 | 0.033 | 0.033 |
| Fragrance | 0.3 | 1 | 0.3 | 0.3 | 1 | 0.3 | 1 | 1 |
| Na EDTA | 0.1 | 0.1 | 0.1 | 0.1 | 0.1 | 0.1 | 0.1 | 0.1 |
| HC Base (20% EDGS) | 3 | — | 3 | 3 | 3 | 3 | 2 | 2 |
| Euperlan (15% EDGS) | — | 1 | — | — | — | — | — | — |
| Polyuquat-10 | 0.1 | — | 0.1 | 0.1 | — | 0.1 | — | — |
| JR 400 | — | — | — | — | 0.1 | — | — | — |
| Beads | — | — | — | — | — | — | — | — |
| Citric Acid | 0.15 | 0.15 | 0.15 | 0.15 | 0.15 | 0.15 | 0.15 | 0.15 |
| NaCl (20% active) | 8.5 | 3.75 | 8.5 | 15 | 8.5 | 7.5 | 10 | 10 |
| Skin Actives | 0.01 | 0.01 | 0.01 | 0.01 | 0.01 | 0.01 | — | — |
| Dyes | 0.04 | 0.02 | 0.04 | 0.04 | 0.04 | 0.04 | — | — |
| Styrene-Acrylates | — | — | — | — | — | — | — | — |
| Minerals | — | — | — | — | — | — | — | — |
| Product Viscosity (cP) | 9,394 | 9,099 | 5,194 | 19,050 | 11,400 | 6,550 | 23,000 | 23,000 |
| Product Tan Delta (25° C.) | 0.49 | 0.42 | 0.55 | 0.61 | 0.42 | 0.53 | 0.30 | 0.30 |
| Product Tan Delta (10° C.) | 0.48 | 0.36 | 0.35 | 0.37 | 0.43 | 0.45 | 0.36 | 0.34 |

| Ingredient | Inventive Examples | | | | | | |
|---|---|---|---|---|---|---|---|
| | I-9 | I-10 | I-11 | I-12 | I-13 | I-14 | I-15 |
| Water | Q.S. | Q.S. | Q.S. | Q.S. | Q.S. | Q.S. | Q.S. |
| SLE3S (28% active) | 30 | 25 | 25 | 25 | 30 | 30 | 30 |
| CAPB (30% active) | 12 | 8 | 8 | 8 | 12 | 12 | 12 |
| SLS (29% active) | — | — | — | — | — | — | — |
| Sorbitol (70% active) | — | 1.5 | 3 | 4.5 | 0 | 0 | 0 |
| Glycerin | 3 | — | — | — | 1 | 2 | 3 |
| Thixcin | — | — | — | — | — | — | — |
| Sodium Benzoate | 0.25 | 0.25 | 0.25 | 0.25 | 0.25 | 0.25 | 0.25 |
| Methylchloro-isothiazolinone/methyliso-thiaxolinone | 0.033 | 0.033 | 0.033 | 0.033 | 0.033 | 0.033 | 0.033 |
| Fragrance | 1 | 1 | 1 | 1 | 1 | 1 | 1 |
| Na EDTA | 0.1 | 0.1 | 0.1 | 0.1 | 0.1 | 0.1 | 0.1 |
| HC Base (20% EDGS) | 2 | — | — | — | 2 | 2 | 2 |
| Euperlan (15% EDGS) | — | — | — | — | — | — | — |
| Polyuquat-10 | — | — | — | — | — | — | — |
| JR 400 | — | — | — | — | — | — | — |
| Beads | — | — | — | — | — | — | — |
| Citric Acid | 0.15 | 0.15 | 0.15 | 0.15 | 0.15 | 0.15 | 0.15 |
| NaCl (20% active) | 10 | 10 | 10 | 10 | 2.5 | 2.5 | 2.5 |
| Skin Actives | — | — | — | — | — | — | — |
| Dyes | — | — | — | — | — | — | — |
| Styrene-Acrylates | — | — | — | — | — | — | — |
| Minerals | — | — | — | — | — | — | — |
| Product Viscosity (cP) | 20,000 | 9,000 | 10,000 | 8,500 | 3,000 | 3,000 | 3,000 |
| Product Tan Delta (25° C.) | 0.30 | 0.54 | 0.50 | 0.50 | 0.73 | 0.80 | 0.91 |
| Product Tan Delta (10° C.) | 0.33 | 0.49 | 0.52 | 0.45 | 1.04 | 0.91 | 1.00 |

As shown in Table 1, Comparative Examples C-1, C-4 through C-6, and C-11 to C-13 illustrate personal care compositions containing SLS in combination with SLE3S (sodium laureth(3) sulfate), CAPB (cocamidopropyl betaine), and sorbitol. Comparative Examples C-2 and C-7 to C-9 illustrate a personal care composition containing SLE3S and CAPB, but not SLS or a polyol. Comparative Examples C-3, C-10, and C-14 through C-16 illustrate a personal care composition containing SLS, SLE3S, and CAPB, but not a polyol.

Inventive Examples I-1 through I-6, and I-10 through I-12 in Table 2, illustrate personal care compositions containing SLES, CAPB, and sorbitol but not SLS. Inventive Examples I-7 through I-9, and I-13 to I-15 illustrate personal care compositions containing SLES, CAPB and glycerin but not SLS. Inventive Examples I-10 to I-12 illustrate personal care compositions containing SLES, CAPB, and low amounts of sorbitol but not SLS.

Comparing Comparative Examples C-3 to C-4, it appears that the addition of sorbitol alone to personal care compositions containing SLS, SLE3S, and CAPB does not result in stable personal care compositions (i.e. personal care compositions having a tan delta greater than about 0.30 at about 10° C.). Comparing C-2 to C-3, it also appears that the removal of SLS from personal care compositions containing SLE3S and CAPB, but without a polyol, does not result in stable personal care compositions as the resulting composition failed to provide desired rheological properties sought by consumers. For example, C-2 was perceived as too gel-like and difficult to spread on the skin, and therefore not stable.

Finally, comparative Examples C-4 through C-6 illustrate that while increasing the concentration of the viscosity modifier NaCl in personal care compositions containing SLE3S, SLS, CAPB, and sorbitol can enhance the viscosity of the personal care compositions, the inclusion of the viscosity modifier alone does not result in a tan delta greater than 0.30 at about 10° C. for the personal care composition.

Surprisingly, comparing Inventive Examples I-1 to I-6 with Comparative Examples C-2, and C-7 through C-9, illustrate that the inclusion of sorbitol in personal care compositions containing SLE3S and CAPB but not SLS results in personal care compositions with a tan delta greater than 0.30 at about 10° C. The amount of sorbitol by weight of the personal care composition required to stabilize the personal care composition containing SLE3s and CAPB can be under 10% as shown in I-1 through I-6 or even in the range of only about 1.5% to about 4.5% as shown in I-10 through I-12. For example, comparing C-2 to I-2, the addition of approximately 3% sorbitol by weight of the personal care composition to the personal care composition containing SLE3S and CAPB but not SLS, increased the tan delta from about 0.30 at about 10° C. to about 0.36 at about 10° C.

The inclusion of glycerin in personal care compositions containing SLE3S and CAPB but not SLS also results in personal care compositions with a tan delta greater than 0.30 at about 10° C. as seen in Inventive Examples I-7 through I-9 through I-13. Comparing I-7 through I-9 with C-7 through C-9 shows the addition of just about 1% to about 3% glycerin by weight of the personal care composition to the personal care composition containing SLE3S and CAPB but not SLS results in an increase of the tan delta from a range of 0.18 to 0.24 to a range of 0.36 to 0.33.

Comparing I-3 to I-4, it also appears that the viscosity of the stable personal care composition containing SLE3S and CAPB but not SLS can be enhanced by increasing the concentration of the viscosity modifier, NaCl. By comparing I-13 to I-15 with I-7 to I-9, it is also apparent that the viscosity of the stable personal care composition can be enhanced by increasing the viscosity modifier while still retaining a tan delta of 0.30 or more for the personal care composition at 10° C.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid personal care composition comprising:
    i) a primary surfactant comprising an anionic surfactant not sodium lauryl sulfate or ammonium lauryl sulfate;
    ii) a secondary surfactant comprising a zwitterionic surfactant, an amphoteric surfactant, a non-ionic surfactant, or a combination thereof; and
    iii) a polyol which is sorbitol;
    wherein the personal care composition exhibits a tan delta of about 0.30 or more at 10° C.

2. The personal care composition of claim 1, wherein the personal care composition is substantially free of non-ethoxylated alkyl sulfates.

3. The personal care composition of claim 1, wherein the personal care composition is substantially free of sodium lauryl sulfate.

4. The personal care composition of claim 1, further comprising a viscosity modifier selected from the group consisting of magnesium nitrate, trimagnesium phosphate, calcium chloride, sodium carbonate, sodium chloride, sodium aluminum sulfate, disodium phosphate, sodium polymetaphosphate, sodium magnesium succinate, sodium sulfate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, ammonium sulfate, calcium acetate, calcium nitrate, calcium phosphate, calcium sulfate, ferric sulfate, magnesium chloride, magnesium sulfate, alkyl ether sulfate, and mixtures thereof.

5. The personal care composition according to claim 1, wherein the secondary surfactant comprises cocoamidopropyl betaine.

6. The personal care composition of claim 5, wherein the cocoamidopropyl betaine comprises from about 2% to about 5% of the personal care composition by weight.

7. The personal care composition according to claim 1, wherein the polyol comprises from about 0.5% to less than 10% by weight of the personal care composition.

8. The personal care composition of claim 1, wherein the personal care composition comprises from about 0.5% to about 5.0% sorbitol by weight of the personal care composition.

9. The personal care composition according to claim 1, wherein the primary surfactant comprises from about 5% to about 10% by weight of the personal care composition.

10. The personal care composition according to claim 1, wherein the primary surfactant comprises from about 6.4% to about 10% by weight of the personal care composition.

11. The personal care composition according to claim 1, wherein the primary surfactant comprises sodium laureth(n) sulfate, ammonium laureth(n) sulfate, sodium trideceth(n) sulfate, or ammonium trideceth(n) sulfate.

12. The personal care composition according to claim 11, wherein the primary surfactant comprises sodium laureth(3) sulfate.

13. The personal care composition according to claim 1, wherein the personal care composition exhibits a viscosity of about 5,000 cP or more at about 25° C.

14. The personal care composition according to claim 1, wherein the personal care composition exhibits a tan delta of about 0.33 or more at about 10° C.

15. The personal care composition according to claim 1, wherein the personal care composition exhibits a tan delta of about 0.35 or more at about 10° C.

16. A liquid personal care composition comprising:
   i) a primary surfactant comprising sodium laureth (3) sulfate;
   ii) a secondary surfactant comprising a zwitterionic surfactant, an amphoteric surfactant, a non-ionic surfactant, or a combination thereof;
   iii) a viscosity modifier; and
   iv) sorbitol comprising from about 0.5% to less than 10% by weight of the personal care composition;
   wherein the personal care composition exhibits a tan delta of about 0.35 or more at about 10° C. and is substantially free of sodium lauryl sulfate.

* * * * *